(12) United States Patent
Bocionek et al.

(10) Patent No.: US 8,291,336 B2
(45) Date of Patent: Oct. 16, 2012

(54) MEDICAL SYSTEM ARCHITECTURE WITH AN INTEGRATED RIS CLIENT ON THE CONSOLE COMPUTER OF A MODALITY

(75) Inventors: Siegfried Bocionek, Nuremberg (DE); Heiderose Pfaff, Erlangen (DE); Detlef Becker, Möhrendorf (DE); Karlheinz Dorn, Kalchreuth (DE); Gerold Herold, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 2866 days.

(21) Appl. No.: 09/994,184

(22) Filed: Nov. 26, 2001

(65) Prior Publication Data

US 2002/0085026 A1   Jul. 4, 2002

(30) Foreign Application Priority Data

Nov. 24, 2000   (DE) .................................. 100 58 396
Nov. 9, 2001   (DE) .................................. 101 54 740

(51) Int. Cl.
*G06F 3/048* (2006.01)
(52) U.S. Cl. ................. 715/771; 715/764; 705/2; 705/3; 600/529
(58) Field of Classification Search .................. 345/764, 345/771; 705/2, 3; 600/529, 533; 715/764, 715/771
See application file for complete search history.

(56) References Cited

U.S. PATENT DOCUMENTS

| 5,654,555 | A | 8/1997 | Buytaert et al. |
| 6,011,552 | A | 1/2000 | Ramanathan et al. |
| 6,210,327 | B1 * | 4/2001 | Brackett et al. ............... 600/437 |
| 6,271,536 | B1 * | 8/2001 | Buytaert et al. .............. 250/584 |
| 6,359,628 | B1 * | 3/2002 | Buytaert ...................... 345/619 |
| 6,578,002 | B1 * | 6/2003 | Derzay et al. .................... 705/2 |

FOREIGN PATENT DOCUMENTS

| DE | 196 25 835 | 2/1998 |
| WO | WO 00/31673 | 2/2000 |

OTHER PUBLICATIONS

"Bildgebende Systeme für die Medizinische Diagnostik", 3rd Ed. (1995) pp. 684-697.

* cited by examiner

*Primary Examiner* — Sara England
(74) *Attorney, Agent, or Firm* — Schiff Hardin LLP

(57) ABSTRACT

In a medical system architecture having a modality for the acquisition of examination images, a device allocated to the modality for processing the examination images, a device for the transmission of data and the examination images and a device for storing the data and examination images, the device for processing the examination images is fashioned as an RIS client for the exchange of text messages as well as for the display of an RIS client window and for the creation of RIS interaction masks, and is connected via a network connection of the devices to an RIS server for communication with the RIS client on the devices.

11 Claims, 5 Drawing Sheets

MEDICAL SYSTEM ARCHITECTURE WITH AN INTEGRATED RIS CLIENT ON THE CONSOLE COMPUTER OF A MODALITY

BACKGROUND OF THE INVENTION

1. Field of the Invention

The present invention is directed to a medical system architecture of the type having a modality for the acquisition of examination images, a device allocated to the modality for processing the examination images, a device for the transmission of data and the examination images and with a device for storing the data and examination images.

2. Description of the Prior Art

Medical system architectures, referred to as PACS (Picture Archival and Communication Systems), wherein image viewing and image processing stations, referred to as workstations, are connected to one another via an image communication network are known from the book, "Bildgebende Systeme fur die medizinische Diagnostik," edited by H. Morneburg, $3^{rd}$ Edition, 1995, pages 684 ff.

The client software of a radiology information system (RIS) is the operating interface for medical-technical radiology assistants (MTRA) or X-ray technicians and physicians in radiology in order, for example, to admit patients, plan and terminate the examinations, administer the findings and initiate billing. Dependent on the embedding in the higher-ranking hospital information system (HIS), some of these procedures can have already ensued in the HIS, for instance the patient admission, performance request and billing, whereby the RIS merely accepts the data coupled to these procedures via a network interface.

In addition to these "administrative activities", the RIS also often functions as workflow driver in radiology in order, for example, to send request data in the form of a DICOM work list entry to a modality such as a CT, MR or X-ray apparatus at which the examination is to occur. Given today's systems, the examination data, for example number of images, series and radiation protection data such as tube voltage (kV), mAs product (mAs), time (s), energy dose (Gy), etc., must be manually read by a worker and transmitted into the RIS for the required transfer of that examination data from the modality into the RIS for documentation and billing, considerable outlay and additional sources of error results therefrom.

When a PACS solution is additionally utilized, then the RIS offers further workflow driver functions, for example in order to automatically load earlier images and findings of a patient from the archive onto a diagnostics workstation, referred to as pre-fetching, or to automatically return images and findings selected according to auto-routing to the requesting clinical departments.

The operation of the RIS ensues via specific client terminals—simple ASCII terminals earlier, currently usually commercially obtainable PCs. This particularly means that an extra personal computer (PC) with its own keyboard is usually located as RIS client next to every console computer of a modality and next to every PACS diagnostics workstation. The operator, for example MTRA or physician, must thereby permanently switch back and forth between the various computers and keyboards. Often, the operator must even undertake double entries of the same data, namely at the console computers of the modality as well as at the terminals of the RIS client. This is especially true of all data that cannot be exchanged standardized via the DICOM work list, for example item counts of consumables or specific work steps that are relevant later in the billing.

Heretofore, the radiological performance could in fact be produced by a number of distributed computers, for example the console computers of the modality and PCs with the RIS client placed next to them, but the operation exhibited only slight user-friendliness for MTRAs and physicians in view of the possibilities of controlling and optimizing the department resources (utilization management) and in view of the possible degree of automation of the information flows.

German OS 196 25 835 discloses a medical system architecture of the type initially described wherein a WWW expansion type (MIME) for images, videos or a viewer of objects of the industrial standard in the WWW browser is allocated to a method for data exchange between various application programs. Further, the scope of the MIME expansion is defined as DICOM images, videos and objects. The basis is thereby formed by an exchange of messages with DICOM via the network interface.

U.S. Pat. No. 5,654,555 is directed to a system for the transmission of X-ray images via a network to a locationally remote device with physical network connections as well as transport protocols and medical protocols, whereby patient examination data can be interrogated from an RIS.

U.S. Pat. No. 6,011,552 discloses a displaceable menu icon for access to an application in a graphic user interface (UI), whereby windows and icons can be arranged in a surveyable manner above one another or next to one another on the picture screen, specifically when one of the windows offers access to a video conferencing session.

SUMMARY OF THE INVENTION

An object of the present invention is to eliminate said weaknesses of the presently standard concept of specific RIS clients as a result of which the operating personnel must switch between "client terminal" and console computers of the modalities, to enhance the user-friendliness, enabling the control and optimization of the department resources (utilization management), and to automate the required information flows.

This object is inventively achieved in a medical system architecture wherein the devices for processing the examination images are fashioned as an RIS client for the exchange of text messages as well as for displaying an RIS client window and for the setup of RIS interaction masks and are connected via a network connection of the devices to an RIS server for the communication with the RIS client on the devices.

The present invention is based on the RIS server communicating with the RIS client on the modality, whereby the RIS client is made available desktop-integrated on the operator console of the modalities.

This ensues in addition to the known DICOM communication. A network interface can be used for this purpose (network card with TCP/IP address), or a second interface can be installed. The present invention is not directed to a mere RIS coupling according to the Prior Art but, in particular, specifies the desktop integration of the RIS client on a modality.

By realizing the RIS client on arbitrary console computers, for example as an RIS window, the RIS function can be operated from the same keyboard without a change in location on the part of user. This is an important advantage of the desktop integration. Additionally, useful new applications can be made available on the console computers of the modalities, particularly in terms of utilization management, i.e. better planning, monitoring and optimization of the work load of the modalities and all participating resources such as personnel, consumables, time and other cost factors. Another advantage is making the functions of the RIS available on the modalities, which will lead to improved automation of the information flow and thus to a speed-up of the process executions in diagnostic radiology. Moreover, as necessary, automatic transfer of the examination data, for example number of studies, images, series, type of sequences and radiation protection data such as tube voltage (kV), mAs product (mAs), time (s), energy dose (Gy), etc., can ensue from the modality into the RIS for documentation and billing. A specification with respect to the consumables employed can also be prescribed from the examination protocol, this merely having to be confirmed, and being correctable as needed.

Due to the integrated RIS client on a console computer of a modality, thus, operation is simplified, the workflow properties are improved and the utilization management functionalities expand.

The described problems can be especially simply solved by the devices for processing the examination images containing an RIS client software, whereby the RIS client software can be integrated into the software and simultaneously integrated into the user interface of the devices by means of desktop integration of radiological modalities.

The integration of the RIS client software into the platform software is especially beneficial since the possibilities of the RIS client software can then be offered in a simple way for all modalities that use this platform software.

Given devices for processing the examination images with monitors, it has proven expedient when a window with the RIS client can be mixed onto the respective monitors next to the examination images in the image processing window.

The devices can be fashioned such that an icon with which the window with the RIS client can be opened is arranged on the user interface.

The RIS client is reproduced quickly and in a simple way on the user interface when the devices are fashioned such that the window with the RIS client is realized as its own task card on the user interface, so that the user merely has to click on the RIS cardfile card tab at the right edge of the picture screen.

The utilitarian value of the inventive devices can be increased when the workflow is controlled by the RIS client for automatic information communication.

Analyses of the frequency of occurrence regarding the effects on the diagnosis quality, or the therapy decision resulting therefrom that are caused by the examination for particular clinical questions can be achieved when the RIS client supplies data for outcome analyses on the console computer of a modality.

A better planning, monitoring and optimization of the work load of the modalities and of all participating resources can be achieved when the RIS client comprises a statistics module for interpretations of collected data.

DESCRIPTION OF THE PREFERRED EMBODIMENTS

Figure 1:
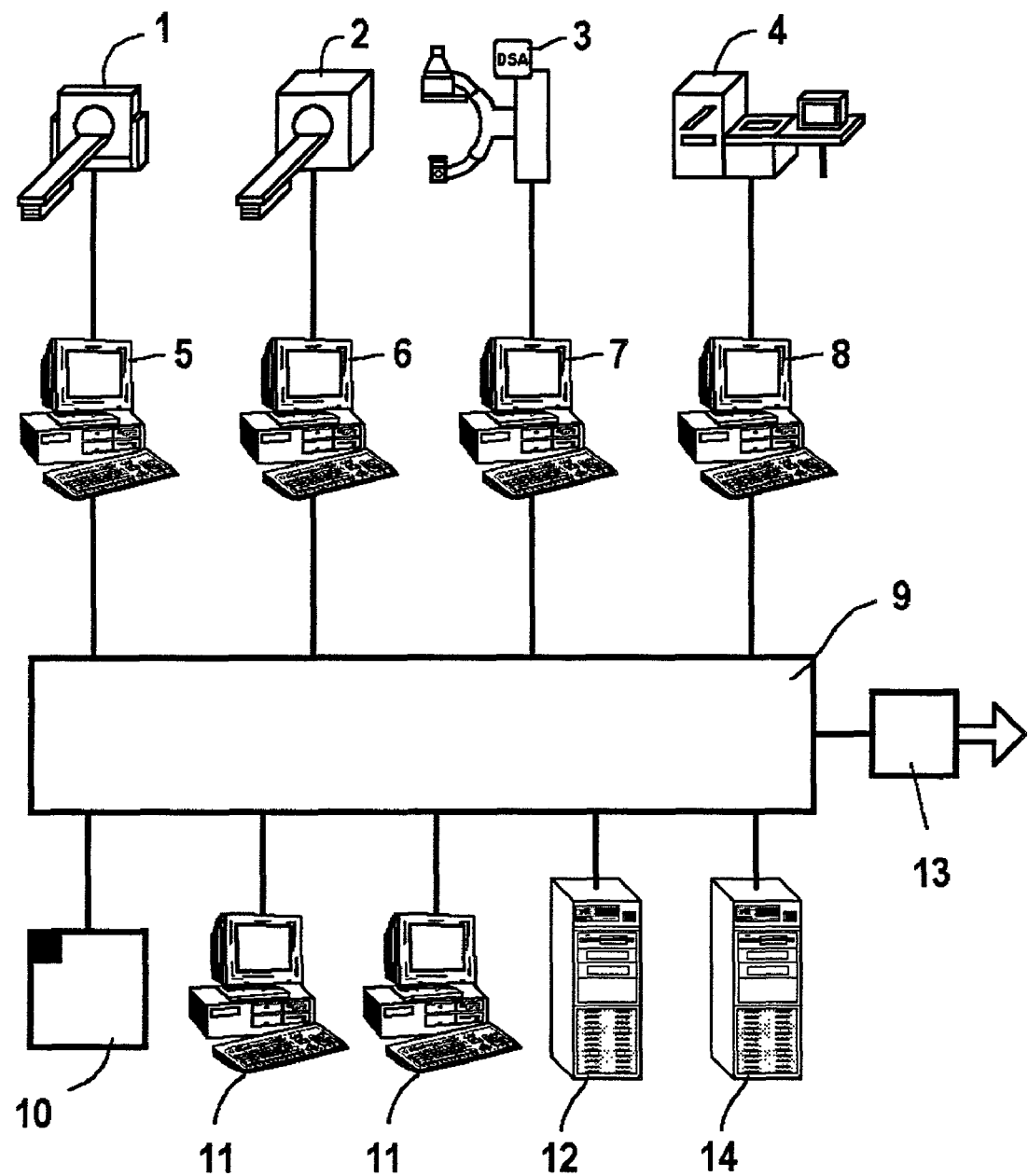
FIG. 1 schematically illustrates an example of a system architecture of a hospital network in which the invention can be employed.

FIG. 1 shows the system architecture of a hospital network by way of example. The modalities 1 through 4 serve for the acquisition of medical images; these can, for example, be a CT unit I for computed tomography, an MR unit 2 for magnetic resonance imaging, a DSA unit 3 for digital subtraction angiography and an X-ray unit 4 for digital radiography 4 as image-generating systems. Operator consoles 5 through 8 (workstations) of the modalities are connected to these modalities, the acquired medical images being capable of being processed and locally stored therewith. Patient data belonging to the images can also be entered.

The operator consoles 5 through 8 are connected to a communication network 9 as a LAN/WAN backbone for distributing the generated images and for communication. Thus, for example, the images generated in the modalities 1 through 4 and the images that are further-processed in the operator consoles 5 through 8 can be stored in central image storage and image archiving system 10 or can be forwarded to other workstations.

Further viewing workstations represented nu a workstation 11 are connected to the communication network 9 as diagnostics consoles that have local image memories. For example, such a viewing workstation 11 is a very fast mini computer on the basis of one or more fast processors. The images that are acquired and deposited in the image archiving system 10 can be subsequently called in the viewing workstation 11 for diagnosis and can be deposited in the local image memory, from which they can be immediately available to the diagnostician working at the viewing workstation 11.

Further, servers 12, for example patient data servers (PDS), file servers, program servers and/or EPR servers, are connected to the communication network 9.

The image and data exchange via the communication network 9 ensues according to the DICOM standard, an industry standard for the transmission of images and further medical information between computers, so that a digital communication between diagnosis and therapy devices of different manufacturers is possible. A network interface 13 via which the internal communication network 9 is connected to a global data network, for example the world wide web, can be connected to the communication network 9, so that the standardized data can be exchanged with different networks world-wide.

Inventively, an RIS server 14 is connected to the communication network 9, the operator consoles 5 through 8 communicating therewith with the communication network via TCP/IP protocols.

Figure 2:
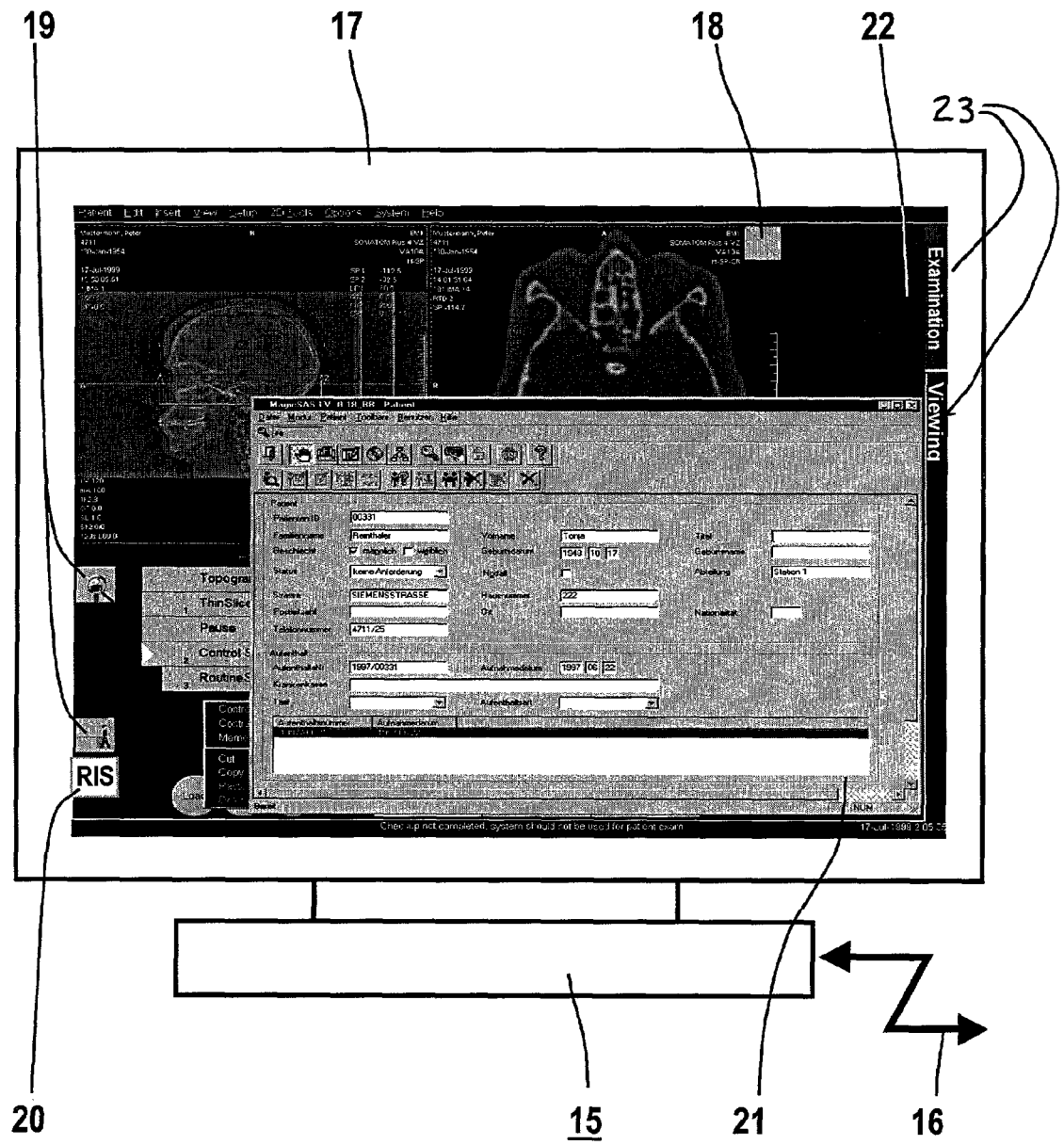
FIG. 2 is a schematic illustration of a monitor of the system architecture with an inventive user interface, for example of a CT with integrated RIS client.

FIG. 2 shows a monitor 15 of a console or backup console computer, for example the operator console 5 of the CT unit 1. The RIS client is connected to the RIS server via a network connection 16 of the operator console 5, but also can communicate with other DICOM-standardized and/or HL7-standardized RIS, HIS and PACS servers 12 by TCP/IP protocol via the internal communication network 9, for example an HIS server for the hospital information system, an EPR server or various PACS serves such as diagnosis consoles, image archive, web im age distribution server, etc. The RIS client uses standard application protocols like DICOM, HL7 but also http in order to reach Internet/Intranet servers.

An image processing window 18, for example the "examination task card", is reproduced on the user interface 17 with a number of CT exposures, next to which icons 19 for triggering commands are arranged in a known way.

Such task cards are known from PCT Application WO 00/31673. User requests or tasks that are to be viewed as an activity of a workflow and that can be advantageously utilized particularly in image post-processing and diagnosis given all imaging methods of medical technology are capable of being selected in a simple and fast way with said task cards. A number of tasks or activities can be processed in parallel and arbitrarily called. The user interface is thereby subdivided into regions, whereby overlays with information of the user request ensue in a control region, fields in the manner of card tabs 23 are arranged at the edge of the user interface, different user requests being respectively allocated to the card tabs 23, and the currently called, current, visible user request being recognizably marked on the card tab 23. The card tabs 23 arranged at the edge according to this card tab concept see to a clear division. A medical workflow is realized therewith.

When inputs are to be made from the CT operator console 5 as an RIS client into the RIS server 14, or when data from the RIS server 14 are to be transmitted into the RIS client (the operator console 5 of the CT unit 1), then an RIS client window 21, for example the picture screen mask for patient registration, is opened on the monitor 15 by clicking on an RIS icon 20 with the mouse. All RIS inputs by MTRA or physician now ensue via the keyboard of the console computer without requiring the operator to go to an extra RIS client terminal. The operator can also unproblematically switch between the image processing window 18 and the RIS client window 21.

Figure 3:
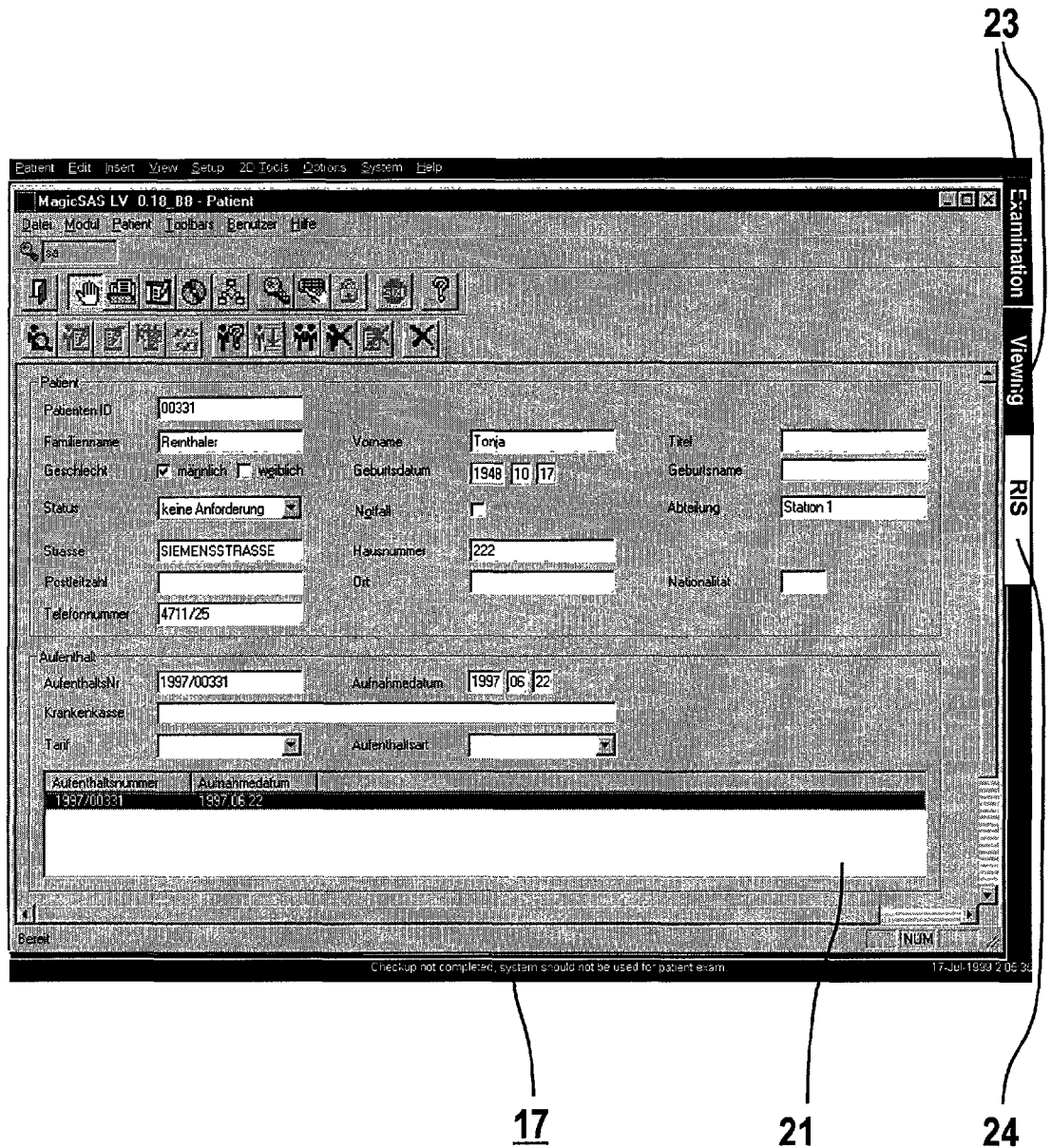
FIG. 3 illustrates a further embodiment of an inventive user interface.

FIG. 3 shows an alternative solution of the desktop integration wherein the RIS client is realized as a separate task card. The user interface of the RIS client appears here when the user clicks on the RIS cardfile card tab 24 at the right edge of the picture screen, so that the RIS client window 21 for patient registration known from FIG. 2 again opens up as task card 22. The subsequent work with the RIS client ensues exactly as in the case of the solution in FIG. 2.

Figure 4:
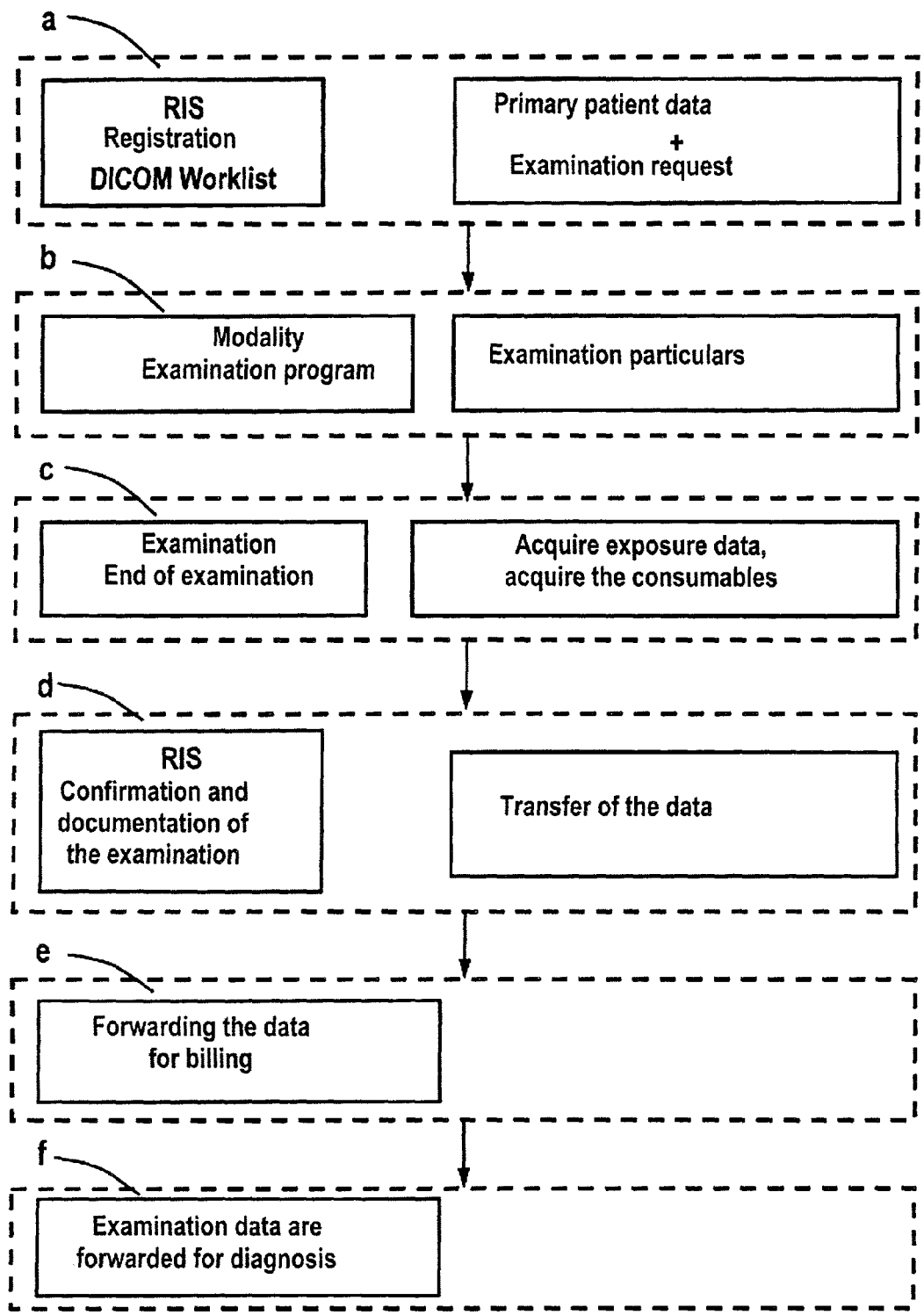
FIG. 4 is a flowchart of a workflow scenario of an inventive apparatus.

FIG. 4 shows a possible workflow scenario of an inventive apparatus. It describes the clinical workflow with the various work steps and the use of the software packets of the various systems such as, for example, the RIS or the modality. The application software employed, the respective software packet/function of the various systems in the sequence of the clinical workflow is shown at the left side, and the data flow is shown at the right side. The data flow is a listing of the data that are utilized by the software packets during the various work steps.

First, the application software of the various systems is described in the sequence of the clinical workflow (left column):
a) First, the patient registration ensues with the RIS and the patient data are automatically transferred into the DICOM work list.
b) After reception of the DICOM work list, these patient data are transmitted in the modality via the work list. Given the selection of a patient, the data and the examination program are loaded according to the question and the examination is started.
c) The examination by the modality ensues.
d) After the end of the examination, the transfer of the examination data to the RIS ensues via DICOM. The confirmation and documentation of the examination ensue here.
e) Next, the data for billing are forwarded to the HIS.
f) The examination data proceed from the modality for further diagnosis, for example at a workstation.

The data flow of the various work steps utilized by the software packets is described in the sequence of the clinical workflow (right column):
a) The patient's primary data and the examination request are acquired or fetched.
b) The examination particulars are input.
c) The exposure data and the consumable are acquired during the examination, for example number of studies, series and images, type of sequences, radiation protection data (kV, mAs, sec., Gy).
d) The data are taken by the RIS.

The simplification of the operation on a single computer with a single keyboard is the directly visible and immediately offered benefit for MTRAs and physicians that follows from the desktop integration of the RIS client on the console computer of a modality.

A further advantage for the efficiency of the work in diagnostic radiology is the possibility of workflow controls from the RIS on the consoles of the modalities such as, for example, the "pre-fetching" and "auto-routing" functions for automatic information transmission. Currently, only exactly one destination node can be pre-defined on a modality for the forwarding of a patient image study or a new destination node must be manually entered each time. This can be made dynamic via the RIS client, i.e. to automatically enable the forwarding of the studies, whereby the destination derives, for example, from the evaluation of the parameters for organ examined, requesting location, information about preliminary diagnosis, etc.

Additional benefits from the integration of the RIS client on the console computer of a modality come to bear when the RIS interface is utilized for better planning, monitoring and optimization of the work load of the modalities and all participating resources such as personnel, consumables, time and other cost factors, i.e. for "utilization management". Each RIS also has a statistics module in which the physician can undertake arbitrary interpretations of the collected data, for example number of different examinations, average examination duration, average use of consumables such as films, contrast agent, nuclides and much more. This statistics module is the point of departure for each utilization management and can now also be utilized on the console computers of the modalities, for example for logging and evaluating which different sequences were applied on an MR in a specific period or which settings such as feed, slice thickness, etc., were selected with what frequency in a multi-slice CT, and what effects these settings had on examination times, and thus on examination costs.

The integration of the RIS client on the console computer of a modality also can become the point of departure for collecting data for outcome analyses. For example, such analyses can investigate which sequences of an MR were selected with which frequency and for which clinical question, and what effect the sequences had on the quality of the diagnosis or on the therapy decision resulting therefrom. The integration of radiological modalities in a comprehensive "disease management" concept is thus enabled long-term.

Figure 5:
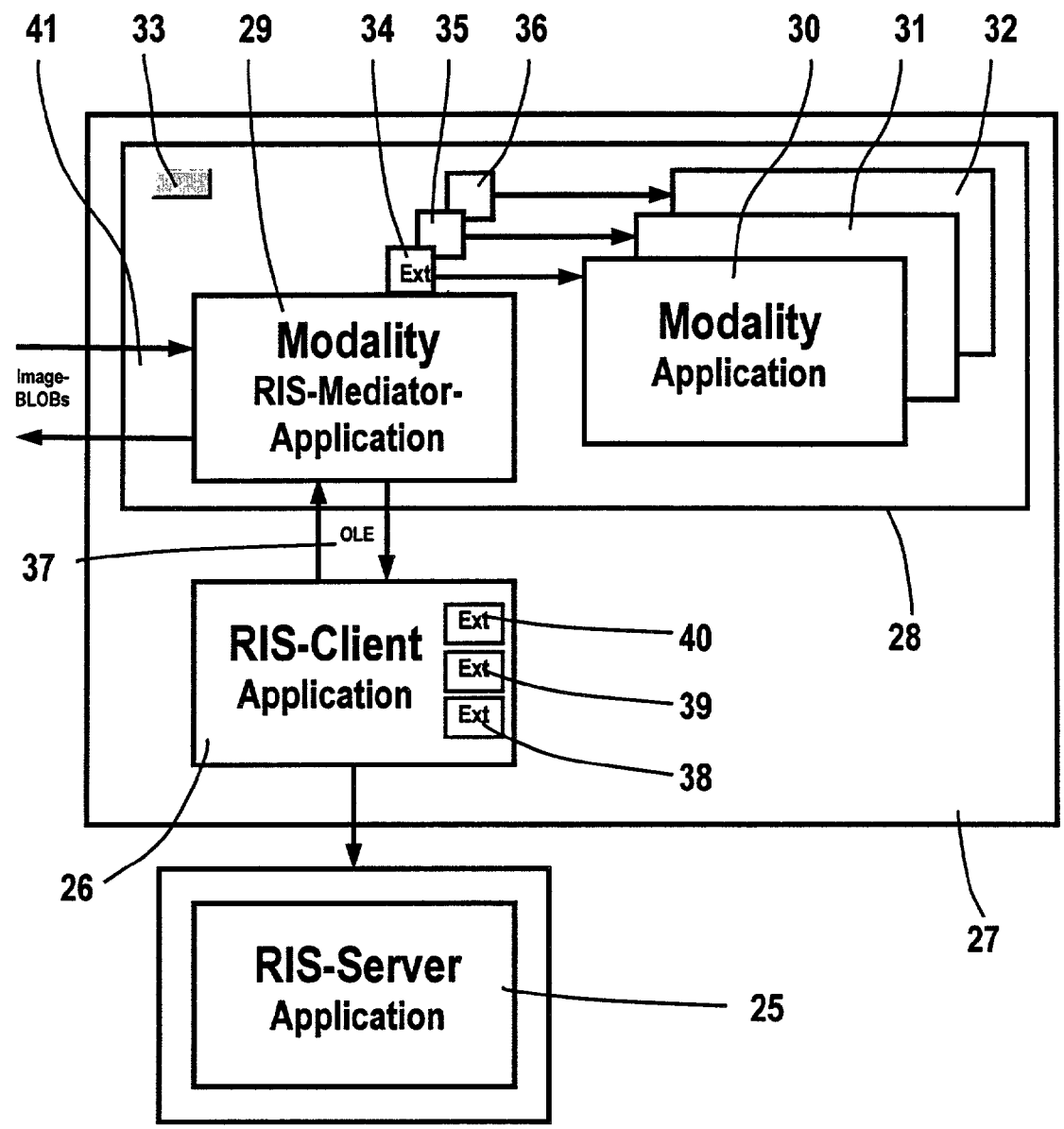
FIG. 5 is a communication scheme between RIS-server and RIS-client on modality console.

The communication of the RIS server with the RIS client is explained in greater detail on the basis of FIG. 5. An RIS server application 25 communicates with an RIS client application 26 that runs on a machine 27. A modality 28 that can comprise a modality-RIS mediator application 29 and modality applications 30 through 32 can also run on the same machine 27.

The modality-RIS mediator application 29 inserts a button 33 for starting the RIS client application 26 into the main menu of the modality 28.

The modality applications 30 through 32 have an extension mechanism 34 through 36 in order to enable an activation for other applications (for example, 30 through 32 or 26) and expands a modality-RIS mediator application 29 therewith.

The modality applications 30 through 32 start an RIS client application 26 with the button 33 from the main menu of the modality 28.

The RIS client application 26 communicates with the modality-RIS mediator applications 29, for example via an OLE protocol 37, and queries its modality application extensions 34 through 36.

The modality-RIS mediator application 29 returns references to its current extensions 34 through 36 via the OLE protocol 37 and what is referred to as a "magic cookie" 38 through 40 for each extension. The RIS client application 26 inserts these into its user interface (UI) for subsequent activation.

When the UI activation of a specific modality application extension 34 through 36 ensues from the RIS client application 26, this is forwarded to the modality-RIS mediator application 29 together with the patient information selected in the RIS client 26 and the "magic cookie" 38 through 40. Via another transport 41, said application 29 attempts to get the necessary image data and forwards them to the respective extensions 34 through 36 that are referenced by the "magic cookie" 38 through 40. The respective extension 34 through 36, finally, transfers the request to the respective modality application 30 through 32.

The request is predetermined for the modality application 30 through 32 by the extensions 34 through 36 and the modality application 30 through 32 can no longer distinguish who ultimately initiated the activation, i.e. a specific mechanism is not required for the RIS client per application.

The modality application 30 through 32 can subsequently load the image data for the diagnosis.

This method can be arbitrarily repeated dynamically at the run time for further modality applications 30 through 32 that can likewise be dynamically activated from the RIS client application 26. It is thus assured that new and existing applications can be automatically connected to the RIS client application 26 and integrated into each modality 28. Further, modality applications 30 through 32 and RIS client application 26 can be modified independently of one another.

The RIS client application 26 usually runs (but not necessarily) on the same machine 27 as the modality 28 and communicates with the information system of the RIS server application 25 via a different transport mechanism in order to connect the patient information of the information system with the modality applications 30 through 32 of a modality 37.

The extensions of the RIS client application 26, the "magic cookies" 38 through 40, make user interface plugins available in the RIS client in order to activate the modality applications 30 through 32 as though the activation had come from another modality application. Here, the modality-RIS mediator application functions as link between RIS client and modality application.

The modality-RIS mediator application is a mediator or link. In this case, it adapts between modality applications—via their extensions to the mediator, since this is constructed like a modality applications—and the RIS client.

Although modifications and changes may be suggested by those skilled in the art, it is the intention of the inventors to embody within the patent warranted hereon all changes and modifications as reasonably and properly come within the scope of their contribution to the art.

We claim as our invention:

1. A medical system architecture comprising:
   a modality for acquiring examination images;
   a processor connected to said modality for processing said examination images;
   a user interface for said processor;
   a transmission system connected to said processor for transmitting said examination images to a location remote from said processor;
   a memory connected to said transmission system for storing said examination images;
   an RIS server; and
   said processor being programmed as an RIS client with an RIS mediator for exchanging text messages and for displaying an RIS client window at said interface and for creating RIS interaction masks at said interface, and prouducing a network connection to said RIS server for communicating with said RIS client to allow transfer of images from said remote location to said processor via said RIS server for general purpose processing and analysis of said images at said processor, using said RIS client window and said RIS interaction masks.

2. A medical system architecture as claimed in claim 1 wherein said processor comprises RIS client software for processing said examination images.

3. A medical system architecture as claimed in claim 2 wherein said processor includes general operating software, and wherein said RIS client software is integrated into said general operating software.

4. A medical system architecture as claimed in claim 2 wherein said processor includes a user interface, and wherein said RIS client software is integrated into said user interface.

5. A medical system architecture as claimed in claim 2 wherein said processor includes platform software, and wherein said RIS client software is integrated into said platform software.

6. A medical system architecture as claimed in claim 1 wherein said processor has a monitor, and wherein said processor is programmed for displaying said examination images on said monitor and for mixing said RIS client window into a display on said monitor next to said examination images.

7. A medical system architecture as claimed in claim 6 wherein said processor displays an icon on said monitor with which said RIS client window can be opened.

8. A medical system architecture as claimed in claim 1 wherein said processor includes a user interface, and wherein said RIS client has a task card allocated thereto on said user interface.

9. A medical system architecture as claimed in claim 1 wherein a workflow associated with acquiring and processing and processing said examination images is controlled by said RIS client for automatic information transmission.

10. A medical system architecture as claimed in claim 1 wherein said processor functions as a control console for said modality, and wherein said RIS client supplies data for analyzing said examination images.

11. A medical system architecture as claimed in claim 1 wherein said RIS client comprises a statistics module for evaluating data associated with said examination images.

* * * * *